United States Patent
Nagai et al.

(10) Patent No.: US 12,102,713 B2
(45) Date of Patent: Oct. 1, 2024

(54) OCULAR SURFACE DRUG RETENTION AGENT, EYE DROP CONTAINING THE SAME, AND METHOD FOR RETENTION OF OCULAR SURFACE DRUG USING THE SAME AND METHOD FOR TREATING OCULAR DISEASE

(71) Applicants: NOF CORPORATION, Tokyo (JP); KINKI UNIVERSITY, Higashiosaka (JP)

(72) Inventors: Noriaki Nagai, Higashiosaka (JP); Shunsuke Sakurai, Kawasaki (JP); Eiji Harata, Kawasaki (JP)

(73) Assignees: NOF CORPORATION, Tokyo (JP); Kinki University, Higashiosaka (JP)

( * ) Notice: Subject to any disclaimer, the term of this patent is extended or adjusted under 35 U.S.C. 154(b) by 0 days.

(21) Appl. No.: 17/903,597

(22) Filed: Sep. 6, 2022

(65) Prior Publication Data

US 2023/0355512 A1    Nov. 9, 2023

(30) Foreign Application Priority Data

Sep. 7, 2021 (JP) ................. 2021-145583
Sep. 5, 2022 (JP) ................. 2022-141056

(51) Int. Cl.
| | |
|---|---|
| *A61K 31/728* | (2006.01) |
| *A61K 9/00* | (2006.01) |
| *A61K 31/4704* | (2006.01) |
| *A61K 31/7084* | (2006.01) |
| *A61P 27/04* | (2006.01) |

(52) U.S. Cl.
CPC ........ *A61K 9/0048* (2013.01); *A61K 31/4704* (2013.01); *A61K 31/7084* (2013.01); *A61K 31/728* (2013.01); *A61P 27/04* (2018.01)

(58) Field of Classification Search
CPC .............. A61K 9/0048; A61K 31/4704; A61K 31/7084; A61K 31/728; A61P 27/04
See application file for complete search history.

(56) References Cited

U.S. PATENT DOCUMENTS

| | | | |
|---|---|---|---|
| 2012/0270955 A1* | 10/2012 | Chowhan ................. | A61K 9/08 514/772.4 |
| 2018/0360872 A1 | 12/2018 | Sakurai et al. | |
| 2019/0218323 A1* | 7/2019 | Edwards ............. | C08F 220/286 |

FOREIGN PATENT DOCUMENTS

WO    2017/110874 A1    6/2017

OTHER PUBLICATIONS

Noriaki Nagai et al., "MPC Polymer Promotes Recovery from Dry Eye via Stabilization of the Ocular Surface"; Pharmaceutics 2021, 13, 168; pp. 1-12.
Poster presentation in Thirty-Sixth Annual Meeting of The Academy of Pharmaceutical Science and Technology, Japan, May 13, 2021.
MPC polymeric solutions; Efficacy in Dry Eye Treatment; Nikkan Kogyo Shimbun; Feb. 7, 2022.
Poster presentation in Japan Cornea Conference 2022 (Feb. 10, 2022).

* cited by examiner

*Primary Examiner* — Zohreh A Fay
(74) *Attorney, Agent, or Firm* — Sughrue Mion, PLLC

(57) ABSTRACT

Provided are an ocular surface drug-retaining agent that enables an excellent improvement in retainability of a medicament on an ocular surface and an eye drop containing the agent. An ocular surface drug-retaining agent containing a copolymer having three different kinds of constituent units at a specific ratio can express an excellent effect of retaining a medicament on an ocular surface (in particular, a corneal surface) to allow the effect or action of the drug to be sustained over a long period of time.

13 Claims, 13 Drawing Sheets

REBAMIPIDE CONCENTRATION

RELATIVE VALUE OF TEAR FILM BREAK-UP AREA

OCULAR SURFACE DRUG RETENTION AGENT, EYE DROP CONTAINING THE SAME, AND METHOD FOR RETENTION OF OCULAR SURFACE DRUG USING THE SAME AND METHOD FOR TREATING OCULAR DISEASE

BACKGROUND OF THE INVENTION

1. Field of the Invention

The present disclosure relates to an ocular surface drug-retaining agent containing a copolymer having a specific structure and an eye drop containing the agent, and to a method of retaining a drug on an ocular surface and a method of treating an ocular disease each using those agents.

The present application claims priority from Japanese Patent Application No. 2021-145583 and Japanese Patent Application No. 2022-141056, which are incorporated herein by reference.

2. Description of the Related Art

An eye drop is known to be a highly effective treatment method while being able to be simply used. Accordingly, various eye drops have been developed and put to good use in treatment for various ocular diseases, such as dry eye and glaucoma.

For example, a Mucosta ophthalmic solution (dry eye therapeutic drug: rebamipide) is used as a dry eye therapeutic drug, and a Timoptol ophthalmic solution (glaucoma therapeutic drug: timolol maleate) is used as a glaucoma therapeutic drug in some cases. When any such ophthalmic solution is used for treatment, in general, instillation needs to be performed from about 2 times to about 4 times a day, and a treatment period may span a long period of, for example, from several weeks to several years.

For the purpose of reducing a burden on a patient, development has been made on an eye drop capable of reducing the number of times of instillation by sustaining an effect of a drug.

As a technology for sustaining an effect of a drug, there have been developed, for example, a technology involving blending a thickener into an eye drop to obtain a high-viscosity eye drop, to thereby retain a drug on an ocular surface (Japanese Patent Application Laid-open No. 2006-89460), and a technology in which, although an eye drop itself has a low viscosity, the eye drop senses a concentration/pH of an ion present on an ocular surface to have a high viscosity after being instilled, to thereby retain a drug on the ocular surface (Japanese Patent Translation Publication No. 2014-525891). In addition, there has also been developed, for example, a technology involving blending a plurality of kinds of pharmacologically active components to further enhance their efficacy, to thereby sustain a pharmacological effect (Japanese Patent Application Laid-open No. 2021-046394).

However, currently, no satisfactory technology has been developed yet as a technology for retaining a medicament efficacious against an ocular disease on an ocular surface or a corneal surface to sustain an effect to be originally expressed over a long period of time.

SUMMARY OF THE INVENTION

With regard to ocular diseases, there is currently a demand for an eye drop capable of retaining an active ingredient on an ocular surface or a corneal surface to sustain its effect or action over a long period of time.

The present disclosure provides an ocular surface drug-retaining agent that enables an excellent improvement in retainability of a medicament on an ocular surface and an eye drop containing the agent, and a method of retaining a drug on an ocular surface and a method of treating an ocular disease each using those agents.

The inventors have made extensive investigations in order to solve the above-mentioned problem, and as a result, have found that an ocular surface drug-retaining agent containing a copolymer having three different kinds of constituent units at a specific ratio can express an excellent effect of retaining a medicament on an ocular surface (in particular, a corneal surface) to allow the effect or action of the drug to be sustained over a long period of time. Thus, the inventors have completed the present disclosure.

That is, the present disclosure is as described below. 1. An ocular surface drug-retaining agent, containing 0.001 w/v % to 1.0 w/v % of a copolymer (P) which contains constituent units represented by the following general formulae (1a) to (1c), has a weight-average molecular weight of from 5,000 to 2,000,000, and has a ratio among the constituent units [(1a)/(1b)/(1c)] of 100/from 10 to 400/from 2 to 50:

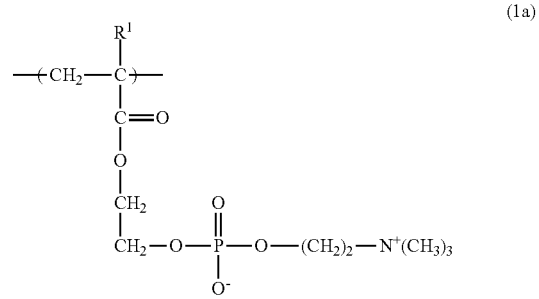

in the general formula (1a), $R^1$ represents a hydrogen atom or a methyl group;

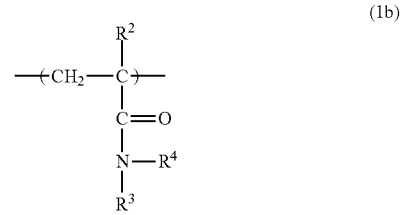

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and

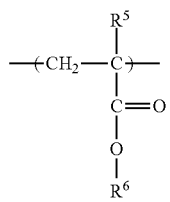
(1c)

in the general formula (1c), $R^5$ represents a hydrogen atom or a methyl group, and $R^6$ represents a hydrocarbon group having 12 to 24 carbon atoms.

2. An eye drop, containing the ocular surface drug-retaining agent of the above-mentioned item 1.

3. The ocular surface drug-retaining agent according to the above-mentioned item 1, wherein the ocular surface drug-retaining agent is administered in combination with an eye drop for treating an ocular disease.

4. The ocular surface drug-retaining agent according to the above-mentioned item 1, wherein the ocular surface drug-retaining agent is administered after the eye drop for treating an ocular disease is administered.

5. The ocular surface drug-retaining agent according to the above-mentioned item 1 or 3, wherein the constituent unit represented by the general formula (1b) is N,N-dimethylacrylamide, and wherein the constituent unit represented by the general formula (1c) is stearyl methacrylate.

6. A dry eye therapeutic agent, containing: the ocular surface drug-retaining agent of the above-mentioned item 5; and one of rebamipide, diquafosol sodium, or sodium hyaluronate.

7. A method of retaining a drug on an ocular surface, including administering, to a mammal including a human, an eye drop for treating an ocular disease, and a composition containing 0.001 w/v % to 1.0 w/v % of a copolymer (P) which contains constituent units represented by the following general formulae (1a) to (1c), has a weight-average molecular weight of from 5,000 to 2,000,000, and has a ratio among the constituent units [(1a)/(1b)/(1c)] of 100/from 10 to 400/from 2 to 50:

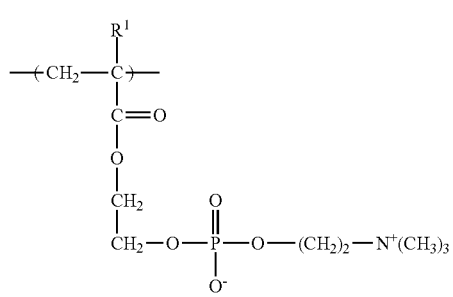
(1a)

in the general formula (1a), $R^1$ represents a hydrogen atom or a methyl group;

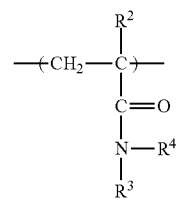
(1b)

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and

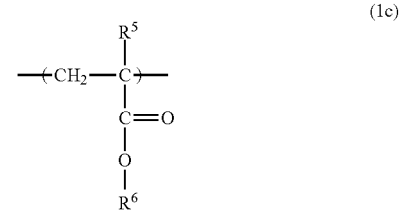
(1c)

in the general formula (1c), $R^5$ represents a hydrogen atom or a methyl group, and $R^6$ represents a hydrocarbon group having 12 to 24 carbon atoms.

8. The method of retaining a drug on an ocular surface according to the above-mentioned item 7, wherein the composition is administered after the eye drop for treating an ocular disease is administered.

9. The method of retaining a drug on an ocular surface according to the above-mentioned item 7, wherein the eye drop for treating an ocular disease is rebamipide.

10. The method of retaining a drug on an ocular surface according to the above-mentioned item 7, wherein the eye drop for treating an ocular disease is diquafosol sodium.

11. The method of retaining a drug on an ocular surface according to the above-mentioned item 7, wherein the eye drop for treating an ocular disease is sodium hyaluronate.

12. A method of treating an ocular disease, including administering, to a mammal including a human, an eye drop for treating an ocular disease, and a composition containing 0.001 w/v % to 1.0 w/v % of a copolymer (P) which contains constituent units represented by the following general formulae (1a) to (1c), has a weight-average molecular weight of from 5,000 to 2,000,000, and has a ratio among the constituent units [(1a)/(1b)/(1c)] of 100/from 10 to 400/from 2 to 50:

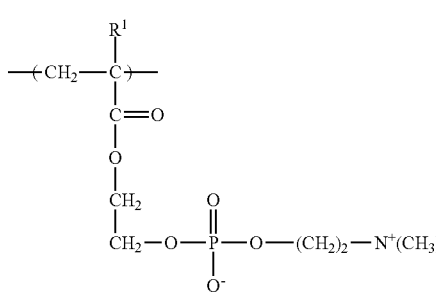
(1a)

in the general formula (1a), $R^1$ represents a hydrogen atom or a methyl group;

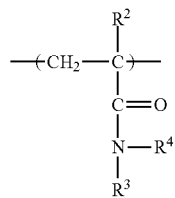
(1b)

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and

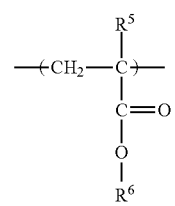
(1c)

in the general formula (1c), $R^5$ represents a hydrogen atom or a methyl group, and $R^6$ represents a hydrocarbon group having 12 to 24 carbon atoms.

13. The method of treating an ocular disease according to the above-mentioned item 12, wherein the composition is administered after the eye drop for treating an ocular disease is administered.

14. The treatment method according to the above-mentioned item 12, wherein the eye drop for treating an ocular disease is rebamipide, and wherein the ocular disease is dry eye.

15. The treatment method according to the above-mentioned item 12, wherein the eye drop for treating an ocular disease is diquafosol sodium, and wherein the ocular disease is dry eye.

16. The treatment method according to the above-mentioned item 12, wherein the eye drop for treating an ocular disease is sodium hyaluronate, and wherein the ocular disease is dry eye.

17. The dry eye therapeutic agent according to the above-mentioned item 6, wherein the dry eye is short tear film break-up time-type dry eye.

BRIEF DESCRIPTION OF THE DRAWINGS

(FIG. 4A), which is room temperature, and 37° C. (FIG. 4B), which is around a body temperature. "MPCP" represents an ophthalmic solution serving as a solution of this Example (ocular surface drug-retaining agent), "DIQ" represents an eye drop containing an ophthalmic medicament (diquafosol sodium ophthalmic solution), and "HYA" represents an eye drop containing an ophthalmic medicament (sodium hyaluronate ophthalmic solution).

FIG. 5A and FIG. 5C show tear film break-up areas after 2 days from instillation, and FIG. 5B and FIG. 5D show tear film break-up areas after 5 days from instillation. For "Saline", instillation treatment was performed with saline. For "DIQ", instillation treatment was performed with an eye drop containing diquafosol sodium (diquafosol sodium ophthalmic solution), and for "DIQ+MPCP", instillation treatment was performed with the diquafosol sodium ophthalmic solution and an ophthalmic solution serving as a solution of this Example (ocular surface drug-retaining agent) in the stated order. For "HYA", instillation treatment was performed with an eye drop containing hyaluronic acid (Hyalein ophthalmic solution), and for "HYA+MPCP", instillation treatment was performed with the Hyalein ophthalmic solution and the ophthalmic solution serving as the solution of this Example (ocular surface drug-retaining agent) in the stated order.

FIG. 6A and FIG. 6C show mucin levels in tears after 2 days from instillation, and FIG. 6B and FIG. 6D show mucin levels in tears after 5 days from instillation. For "Saline", instillation treatment was performed with saline. For "DIQ", instillation treatment was performed with an eye drop containing diquafosol sodium (diquafosol sodium ophthalmic solution), and for "DIQ+MPCP", instillation treatment was performed with the diquafosol sodium ophthalmic solution and an ophthalmic solution serving as a solution of this Example (ocular surface drug-retaining agent) in the stated order. For "HYA", instillation treatment was performed with an eye drop containing hyaluronic acid (Hyalein ophthalmic solution), and for "HYA+MPCP", instillation treatment was performed with the Hyalein ophthalmic solution and the ophthalmic solution serving as the solution of this Example (ocular surface drug-retaining agent) in the stated order.

DESCRIPTION OF THE EMBODIMENTS

Figure 1:
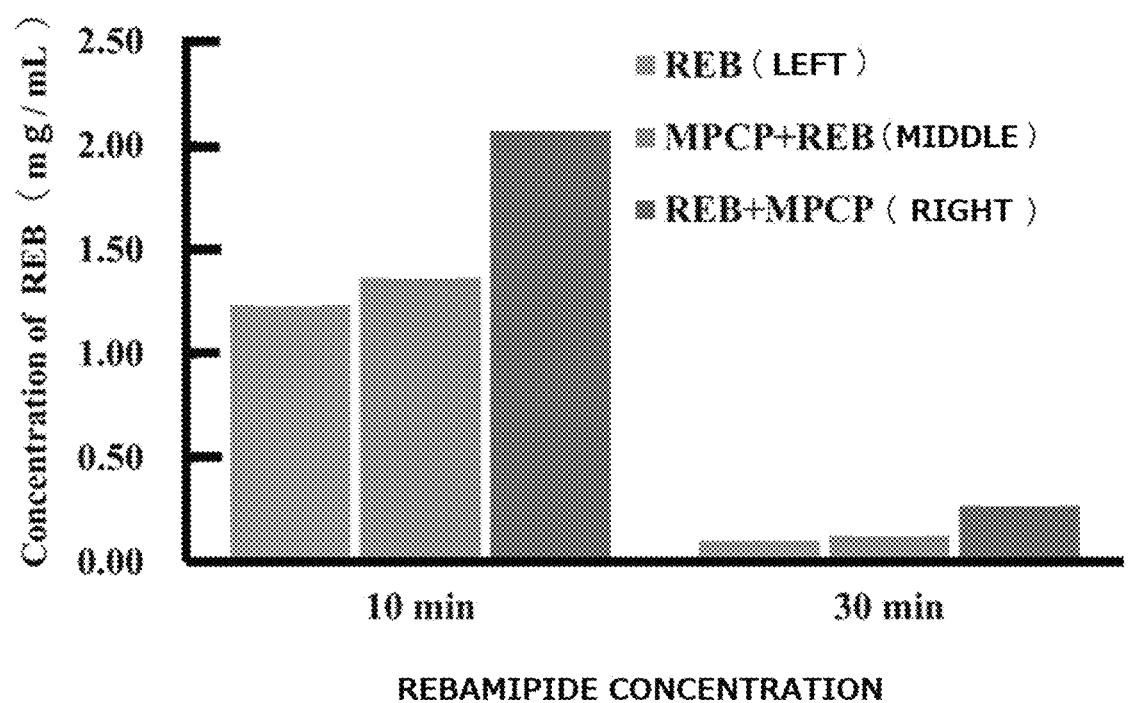
FIG. 1 shows the results of a drug ocular surface retainability test. Rebamipide (REB) concentrations on an ocular surface after 10 minutes and after 30 minutes from instillation were measured. For "REB (left side)", treatment was performed with an eye drop containing an ophthalmic medicament (rebamipide ophthalmic solution). For "MPCP+REB (middle)", instillation treatment was performed with an ophthalmic solution serving as a solution of this Example (ocular surface drug-retaining agent) and the rebamipide ophthalmic solution in the stated order. For "REB+MPCP (right side)", instillation treatment was performed with the rebamipide ophthalmic solution and the ophthalmic solution serving as the solution of this Example (ocular surface drug-retaining agent) in the stated order.

The present disclosure is described in more detail below.

An ocular surface drug-retaining agent of the present disclosure contains a copolymer (P) which contains constituent units represented by the following general formulae (1a) to (1c), and which has a weight-average molecular weight of from 5,000 to 2,000,000. The concentration of the copolymer (P) in the ocular surface drug-retaining agent is from 0.001 w/v % to 1.0 w/v %. In addition, the ratio (molar ratio) among the constituent units [(1a)/(1b)/(1c)] in the copolymer (P) is 100/from 10 to 400/from 2 to 50.

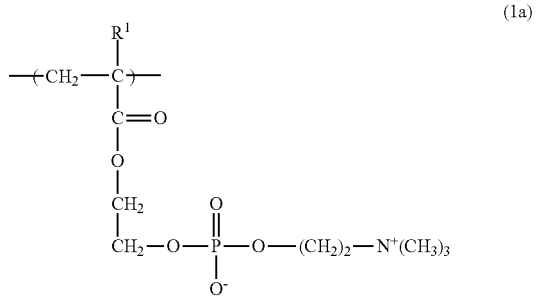
(1a)

In the general formula (1a), $R^1$ represents a hydrogen atom or a methyl group.

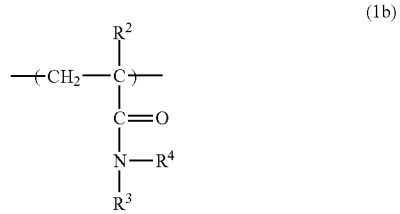
(1b)

In the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other.

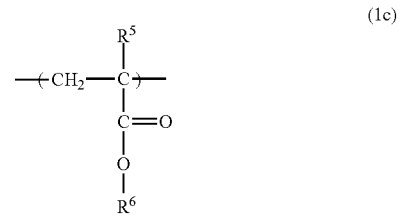
(1c)

In the general formula (1c), $R^5$ represents a hydrogen atom or a methyl group, and $R^6$ represents a hydrocarbon group having 12 to 24 carbon atoms.

As used herein, the term "(meth)acrylate" means "acrylate or methacrylate", and the same applies to other similar terms.

Herein, when preferred numerical ranges (e.g., the ranges of a concentration or a weight-average molecular weight) are described in stages, the respective lower limit values and upper limit values may be independently combined with each other. For example, in the description: "preferably 10 or more, more preferably 20 or more, and preferably 100 or less, more preferably 90 or less", the "preferred lower limit value: 10" and the "more preferred upper limit value: 90" may be combined to obtain a range of "10 or more and 90 or less". In addition, for example, also in the description: "preferably from 10 to 100, more preferably from 20 to 90", a range of "from 10 to 90" may be similarly obtained.

<Copolymer (P)>

The copolymer (P) to be used (contained) in the ocular surface drug-retaining agent of the present disclosure contains the constituent units represented by the general formulae (1a) to (1c), and has a weight-average molecular weight of from 5,000 to 2,000,000.

[Constituent Unit Represented by General Formula (1a)]

The copolymer (P) to be used in the present disclosure has the constituent unit represented by the following general formula (1a), that is, a constituent unit having a phosphorylcholine structure (hereinafter sometimes referred to as "PC constituent unit"). By virtue of the copolymer (P) having the PC constituent unit, an excellent action of retaining a drug on an ocular surface or a corneal surface can be imparted to the copolymer (P).

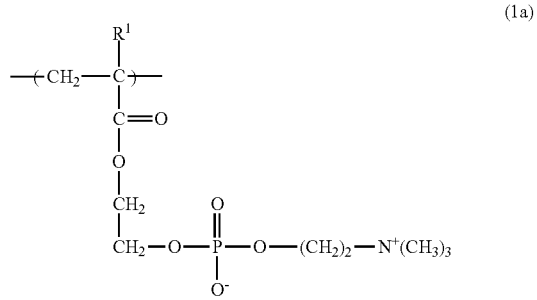
(1a)

In the general formula (1a), $R^1$ represents a hydrogen atom or a methyl group.

As a PC monomer, for example, 2-((meth)acryloyloxy)ethyl-2'-(trimethylammonio)ethyl phosphate is preferred from the viewpoint of availability, and 2-(methacryloyloxy)ethyl 2-(trimethylammonio)ethyl phosphate represented by the following formula (1a') (hereinafter sometimes referred to as "2-methacryloyloxyethyl phosphorylcholine") is more preferred.

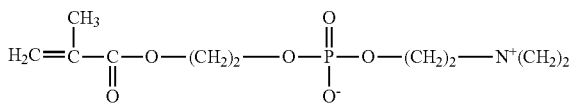
(1a')

[Constituent Unit Represented by General Formula (1b)]

The copolymer (P) to be used in the present disclosure has the constituent unit represented by the following general formula (1b) (hereinafter sometimes referred to as "amide constituent unit"). By virtue of increasing the molecular weight of the copolymer (P) with the amide constituent unit, the retainability of the copolymer (P) on an ocular surface or a corneal surface can be improved.

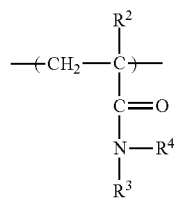
(1b)

In the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other.

The amide constituent unit is a monomer represented by the following general formula (1b') (hereinafter sometimes referred to as "amide monomer"), and may be obtained by copolymerizing (meth)acrylamide or a (meth)acrylamide derivative.

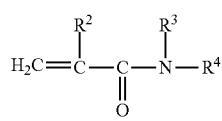
(1b')

$R^2$, $R^3$, and $R^4$ in the general formula (1b') each have the same meaning as that in the general formula (1b).

Specific examples of the monomer represented by the formula (1b') include N,N-dimethyl(meth)acrylamide, N,N-diethyl(meth)acrylamide, and N-acryloylmorpholine. Of those, N,N-dimethylacrylamide is preferred.

In the copolymer (P), when the number of the PC constituent units is set to 100, the ratio [(1a)/(1b)] of the number of the PC constituent units (1a) to the number of the amide constituent units (1b) is 100/from 10 to 400, preferably 100/from 30 to 250, more preferably 100/from 50 to 150, still more preferably 100/from 70 to 120, yet still more preferably 100/from 80 to 110, most preferably 100/from 80 to 100.

When 1b is excessively large, there is a risk in that aseptic filtration to be needed in the production of the eye drop may become difficult, and when 1b is excessively small, the surface drug-retaining effect cannot be expected.

When the ratio of the number of the amide constituent units to the number of the PC constituent units is excessively large, there is a risk in that the aseptic filtration to be performed in the production of the ocular surface drug-retaining agent of the present disclosure may become difficult. Meanwhile, when the ratio is excessively small, the increase in molecular weight of the copolymer (P) becomes insufficient, resulting in a risk in that the retaining effect of the copolymer (P) on an ocular surface or a corneal surface may become insufficient.

[Constituent Unit Represented by General Formula (1c)]

The copolymer (P) to be used in the present disclosure has the constituent unit represented by the following general formula (1c) (hereinafter sometimes referred to as "hydrophobic constituent unit"). By virtue of the copolymer (P) having the hydrophobic constituent unit, the adhesiveness of the copolymer (P) to an ocular surface or a corneal surface can be improved, and besides, its ability to form a physically crosslinked gel through a hydrophobic interaction can be enhanced to further enhance the retainability of a drug on an ocular surface or a corneal surface exhibited by the copolymer (P).

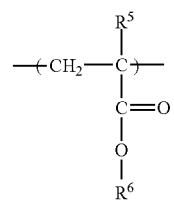
(1c)

In the general formula (1c), $R^5$ represents a hydrogen atom or a methyl group, and $R^6$ represents a hydrocarbon group having 12 to 24 carbon atoms.

$R^6$ in the general formula (1c) represents a hydrocarbon group having 12 to 24 carbon atoms, and may be linear or branched, but is preferably linear. Examples of the hydrocarbon group having 12 to 24 carbon atoms include a lauryl group, a myristyl group, a cetyl group, a stearyl group, an oleyl group, and a behenyl group.

From the viewpoint of improving the adhesiveness of the copolymer (P) to an ocular surface or a corneal surface, $R^6$ represents preferably a hydrocarbon group having 12 to 20 carbon atoms, more preferably a hydrocarbon group having 12 to 18 carbon atoms out of those groups, and specifically, preferably represents a lauryl group or a stearyl group.

The hydrophobic constituent unit may be obtained by polymerizing a monomer represented by the following formula (1c') (hereinafter sometimes referred to as "hydrophobic monomer").

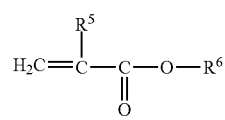
(1c')

$R^5$ and $R^6$ in the general formula (1c') each have the same meaning as that in the general formula (1c).

Specific examples of the hydrophobic monomer represented by the general formula (1c') include linear alkyl (meth)acrylates, such as lauryl (meth)acrylate, myristyl (meth)acrylate, cetyl (meth)acrylate, stearyl (meth)acrylate, oleyl (meth)acrylate, and behenyl (meth)acrylate.

From the viewpoint of improving the adhesiveness of the copolymer (P) to a corneal surface, the hydrophobic monomer represented by the general formula (1c') is preferably lauryl (meth)acrylate, myristyl (meth)acrylate, or stearyl (meth)acrylate, more preferably lauryl methacrylate or stearyl methacrylate, most preferably stearyl methacrylate out of those groups.

In the copolymer (P), when the number of the PC constituent units is set to 100, the ratio [(1a)/(1c)] of the number of the PC constituent units (1a) to the number of the hydrophobic constituent units (1c) is 100/from 2 to 50, preferably 100/from 5 to 25, most preferably 100/from 8 to 15.

When 1c is excessively small, the surface drug-retaining effect is not sufficient, and when 1c is excessively large, the hydrophilicity of the copolymer (P) is reduced to reduce its solubility in an aqueous solution, making it difficult to produce the surface drug-retaining agent.

When the ratio of the number of the hydrophobic constituent units to the number of the PC constituent units is excessively small, there is a risk in that the adhesiveness of the copolymer (P) to an ocular surface or a corneal surface may become insufficient. Meanwhile, when the ratio is excessively large, the hydrophilicity of the copolymer (P) is reduced, and hence its solubility in an aqueous solution is reduced, resulting in a risk in that it may become difficult to produce the ocular surface drug-retaining agent.

From a viewpoint regarding the adhesiveness of a drug to a corneal surface exhibited by the copolymer (P), the ratio (molar ratio) among the constituent units [(1a)/(1b)/(1c)] in the copolymer (P) is 100/from 10 to 400/from 2 to 50, preferably 100/from 30 to 250/from 5 to 25, more preferably 100/from 50 to 150/from 5 to 25, still more preferably 100/from 70 to 120/from 5 to 25, yet still more preferably 100/from 80 to 110/from 7 to 20, yet still more preferably 100/from 80 to 100/from 8 to 15.

The copolymer (P) to be used in the present disclosure only needs to have at least one kind of each of the PC constituent unit, the amide constituent unit, and the hydrophobic constituent unit, and for example, may contain a plurality of kinds of other constituent units.

[Weight-Average Molecular Weight of Copolymer (P)]

The weight-average molecular weight of the copolymer (P) is from 5,000 to 2,000,000, is preferably 10,000 or more, more preferably 20,000 or more, still more preferably 50,000 or more, yet still more preferably 700,000 or more, and is preferably 1,800,000 or less, more preferably 1,600,000 or less, still more preferably 1,500,000 or less, yet still more preferably 1,300,000 or less, yet still more preferably 1,100,000 or less. When the weight-average molecular weight is less than 5,000, there is a risk in that the adhesiveness of the copolymer (P) to an ocular surface or a corneal surface may become insufficient, and there is a risk in that the action of retaining a drug on an ocular surface or a corneal surface cannot be expected. When the weight-average molecular weight is more than 2,000,000, there is a risk in that the viscosity of the ocular surface drug-retaining agent may be increased to make its handling difficult.

The weight-average molecular weight of the copolymer (P) refers to a value according to gel permeation chromatography (GPC) measurement. Specifically, the weight-average molecular weight of the copolymer (P) refers to a molecular weight in terms of polyethylene glycol measured using as an eluent any one of chloroform, dimethylformamide, tetrahydrofuran, methanol, and liquids obtained by combining these solvents.

[Method of Producing Copolymer (P)]

The copolymer (P) may be prepared by, for example, copolymerizing the above-mentioned monomers in accordance with a method described in WO 2013/128633 A1. In addition, the copolymer (P) is generally a random copolymer, but may be an alternate copolymer or block copolymer in which the constituent units are regularly arranged, and may have a graft structure as a part thereof.

[Concentration of Copolymer (P)]

In the ocular surface drug-retaining agent of the present disclosure, the concentration of the copolymer (P) is 0.001 w/v % or more, preferably 0.002 w/v % or more, more preferably 0.003 w/v % or more, still more preferably 0.005 w/v % or more, and is 1.0 w/v % or less, preferably 0.8 w/v % or less, more preferably 0.6 w/v % or less, still more preferably 0.5 w/v % or less.

When the concentration of the copolymer (P) is less than 0.001 w/v %, a sufficient action of retaining a drug on an ocular surface or a corneal surface is not obtained. A concentration of more than 1.0 w/v % is economically disadvantageous because an effect commensurate with the blending amount is not obtained.

In the present disclosure, "w/v %" is an expression of the mass of a given component in 100 ml of a solution in grams (g). For example, the description that "a solution of the present disclosure contains 1.0 w/v % of the copolymer (P)" means that 100 ml of the solution contains 1.0 g of the copolymer (P).

The ocular surface drug-retaining agent of the present disclosure may contain water as required. The water to be used may be water to be generally used in the production of a pharmaceutical or a medical device, but is not particularly limited. Specific examples thereof may include ion-exchanged water, purified water, sterile purified water, distilled water, and water for injection.

[Usage Mode of Ocular Surface Drug-Retaining Agent of the Present Disclosure]

The ocular surface drug-retaining agent of the present disclosure may be used in combination (administered in combination) with a general eye drop for treating an ocular disease. Specifically, a known eye drop for treating an ocular disease is instilled in advance, and then the ocular surface drug-retaining agent of the present disclosure or an eye drop containing the agent is instilled, and thus a drug contained in the known eye drop for treating an ocular disease can be retained on an ocular surface or a corneal surface to sustain the effect/action of the drug over a long period of time.

The eye drop for treating an ocular disease, which is used before the instillation of the ocular surface drug-retaining agent of the present disclosure or the eye drop containing the agent, is not particularly limited, and any eye drop for treating an ocular disease may be used. Specifically, an eye drop having blended therein a drug having pharmacological activity is used, and for example, an eye drop having blended therein an antiallergic drug, a glaucoma therapeutic drug, a dry eye therapeutic drug, an antimicrobial drug, a mydriatic/cycloplegic, a local anesthetic, or the like may be used.

More specific examples of the eye drop for treating an ocular disease, which may be combined with the ocular surface drug-retaining agent of the present disclosure, include eye drops having blended therein the following drugs.

Examples of the antiallergic drug include epinastine hydrochloride, sodium cromoglicate, and pemirolast potassium.

Examples of the glaucoma therapeutic drug include timolol maleate, omidenepag isopropyl, carteolol hydrochloride, dipivefrine hydrochloride, dorzolamide hydrochloride, nipradilol, bunazosin hydrochloride, brimonidine tartrate, brinzolamide, betaxolol hydrochloride, and ripasudil hydrochloride hydrate.

Examples of the dry eye therapeutic drug include rebamipide, diquafosol sodium, and sodium hyaluronate.

Examples of the antimicrobial drug include vancomycin hydrochloride and tobramycin.

An example of the mydriatic/cycloplegic is atropine sulfate hydrate.

An example of the local anesthetic is oxybuprocaine hydrochloride.

Of the eye drops for treating ocular diseases to be combined with the ocular surface drug-retaining agent of the present disclosure, a glaucoma therapeutic drug or a dry eye therapeutic drug is preferred, timolol maleate is preferred as the glaucoma therapeutic drug, and rebamipide, diquafosol sodium, or sodium hyaluronate is preferred as the dry eye therapeutic drug.

A preferred method for combined administration (combined dosage form) of the ocular surface drug-retaining agent of the present disclosure may be as exemplified below, but is not particularly limited.

Administration Interval

After the known eye drop for treating an ocular disease has been administered, the ocular surface drug-retaining agent of the present disclosure is administered from 0.1 minute to 60 minutes later, preferably from 0.2 minute to 30 minutes later, more preferably from 0.3 minute to 20 minutes later.

Dose

The dose of the ocular surface drug-retaining agent of the present disclosure is from 0.05 to 10,000, preferably from 0.1 to 10,000, more preferably from 1 to 6,000 when the dose of the known eye drop for treating an ocular disease is defined as 100 (when specified with their active ingredients having the same concentration).

An administration method in each of a method of retaining a drug on an ocular surface and a method of treating an ocular disease of the present disclosure is not particularly limited. For example, no particular limitation is imposed as long as the known eye drop for treating an ocular disease and the ocular surface drug-retaining agent of the present disclosure are administered in combination to a mammal including a human. Specifically, it is preferred that, after the known eye drop for treating an ocular disease has been administered, 0.01 mL to 0.2 mL of the ocular surface drug-retaining agent of the present disclosure be dropped onto an eye (eyeball) from any angle, from 1 to 10 times, from 1 to 8 times, from 1 to 6 times, from 1 to 4 times, or from 1 to 3 times (preferably in the morning, the afternoon, and the evening) a day.

A target to be treated, which is not particularly limited, is a mammal including a human, and the target is preferably a patient in need of prevention, alleviation, amelioration, or treatment of dry eye (in particular, short tear film break-up time-type dry eye).

In short tear film break-up time-type dry eye, for example, a reduction in function of mucin present on a corneal surface or a reduction in absolute mucin level reduces an ability to spread tears over the corneal surface or hold tears thereon, resulting in dry eye symptoms. That is, according to results of Examples described below, the ocular surface drug-retaining agent of the present disclosure, and the method of retaining a drug on an ocular surface and the method of treating an ocular disease each using the agent can be preferably used for the treatment of short tear film break-up time-type dry eye.

[Other Components]

The ocular surface drug-retaining agent of the present disclosure may further contain the following additives as required in addition to the copolymer (P).

Examples of the additives may include additives that have been used for related-art eye drops and the like, and examples thereof include a sugar, a cooling agent, an inorganic salt, an organic acid salt, an acid, a base, an antioxidant, a stabilizing agent, and an antiseptic agent.

Examples of the sugar include glucose, mannitol, sorbitol, xylitol, and trehalose.

Examples of the cooling agent include menthol and camphor.

Examples of the inorganic salt include sodium chloride and potassium chloride.

An example of the organic acid salt is sodium citrate.

Examples of the acid include phosphoric acid, citric acid, sulfuric acid, and acetic acid.

Examples of the base include trishydroxymethylaminomethane and monoethanolamine.

Examples of the antioxidant include tocopherol acetate and dibutylhydroxytoluene.

Examples of the stabilizing agent include sodium edetate and glycine.

Examples of the antiseptic agent include benzalkonium chloride, chlorhexidine gluconate, potassium sorbate, and polyhexanide hydrochloride.

[Method of Producing Ocular Surface Drug-Retaining Agent or Eye Drop Containing the Agent]

The ocular surface drug-retaining agent of the present disclosure or the eye drop containing the agent may be produced by a general method of producing an eye drop, involving mixing and stirring the copolymer (P), water, and as required, other components. As required, the eye drop is subjected to an operation such as aseptic filtration.

EXAMPLES

The present disclosure is specifically described by way of Examples below, but the present disclosure is not limited to the scope of the following Examples.

Example 1

[Preparation of Copolymer (P)]

A copolymer (1) described below was used as the copolymer (P). The copolymer (1) was prepared by a method described in Examples of WO 2013/128633 A1.

Copolymer (1)

2-(Methacryloyloxy) ethyl 2-(trimethylammonio) ethyl phosphate (2-methacryloyloxyethyl phosphorylcholine) represented by the formula (1a') was used as a PC monomer, N,N-dimethylacrylamide was used as an amide monomer, and stearyl methacrylate was used as a hydrophobic monomer.

Constituent ratio (molar ratio) among constituent units [(1a)/(1b)/(1c)]=100/90/10

Weight-average molecular weight: 1,000,000

[Weight-average Molecular Weight of Copolymer (1)]

The weight-average molecular weight of the copolymer (1) was measured under the following analysis conditions using a sample solution obtained by dissolving 5 mg of the obtained copolymer in a methanol/chloroform mixed liquid (80/20).

Column: PLgel-mixed-C

Standard substance: polyethylene glycol

Detector: differential refractometer RI-8020 (manufactured by Tosoh Corporation)

Calculation method for weight-average molecular weight: molecular weight calculation program (GPC program for SC-8020)

Flow rate: 1 mL per minute

Injection volume: 100 μL

Column oven: constant temperature around 40° C.

[Test of Drug Retainability on Ocular Surface]

In accordance with the following procedure (reference: Development of Sustained-Release Ophthalmic Formulation Based on Tranilast Solid Nanoparticles. Materials (Basel). 2020 Apr. 3; 13(7): 1675. doi: 10.3390/ma13071675.), various kinds of measurement were performed in order to determine an effect of improving the retainability of a drug on an ocular surface.

Example 2

Retainability Measurement Test of Drug on Ocular Surface (1) A male Japanese white rabbit was subjected to instillation in the following combinations.

(I) 30 μL of a rebamipide ophthalmic solution (manufactured by Otsuka Pharmaceutical Co., Ltd.) serving as a known dry eye therapeutic drug was instilled once.

(II) 30 μL of a solution containing the copolymer (1) (An aqueous solution containing 1 w/v % of the copolymer (1) was prepared in advance, and 0.1 mL thereof and saline (sodium chloride: 0.9%, water: balance) were used to prepare a solution containing 0.1 w/v % of the copolymer (1).) was instilled once, and 5 minutes later, 30 μL of the rebamipide ophthalmic solution was instilled once.

(III) 30 μL of the rebamipide ophthalmic solution was instilled once, and 5 minutes later, 30 μL of the solution containing the copolymer (1) was instilled once.

(2) After 10 minutes and after 30 minutes from the second instillation (5 minutes after the first instillation in (I)), rebamipide concentrations in tears were measured by the following method.

Rebamipide Concentration Measurement Test

A prepared REB sample (tears collected with Schirmer test paper) was diluted with N,N-dimethylformamide, and the resultant was placed in a sample bottle (dispensation amount: 150 μL). After that, the sample was analyzed by an HPLC method under the following conditions to measure its REB concentration.

Mobile phase: phosphate buffer/acetonitrile=83/17 (v/v)

Column: column for HPLC filled with octadecylsilylated silica gel; Inertsil ODS-3, GL Sciences Inc.

HPLC apparatus: LabSolution (Shimadzu Corporation)

Column temperature: 35° C.

Flow rate: 0.25 mL/min

Detector: UV detector (254 nm)

Injection amount: 10 μL

Example 3

(Generation of Dry Eye Model)

A dry eye model was generated by the following procedure.

(1) N-Acetylcysteine was dissolved in saline (sodium chloride: 0.9%, water: balance) to prepare a 10 w/v % solution.

(2) The solution prepared in (1) was used and administered by instillation to a male Japanese white rabbit 6 times in total at a single dose of 50 μL and at intervals of 2 hours.

(3) The day after the instillation administration, the dry eye state of the male Japanese white rabbit was recognized, and then the rabbit was used as a dry eye model that had developed dry eye (dry eye model on the 0th day).

Example 4

Determination of Dry Eye Therapeutic Effect through Calculation of Tear Film Break-Up Area A tear film break-up area was calculated by the following procedure.

(1) For the dry eye model of Example 3 (dry eye model on the 0th day), the dry eye state was measured (calculation of tear film break-up area) using a dry eye measurement apparatus (DR-1α, Kowa Company, Ltd.).

(2) After the dry eye measurement (dry eye model on the 0th day), instillation was performed under the following conditions every day for 5 days (dry eye model on the 1st day to the 5th day).

(I) 30 μL of a rebamipide ophthalmic solution (manufactured by Otsuka Pharmaceutical Co., Ltd.) was instilled once.

(II) 30 μL of a solution containing the copolymer (1) was instilled once, and 5 minutes later, 30 μL of the rebamipide ophthalmic solution was instilled once.

(III) 30 μL of the rebamipide ophthalmic solution was instilled once, and 5 minutes later, 30 μL of the solution containing the copolymer (1) was instilled once.

(IV) 30 μL of saline {saline (sodium chloride: 0.9%, water: balance) (manufactured by Otsuka Pharmaceutical Co., Ltd.)} was instilled once.

(3) On the 2nd day from the start of instillation, the dry eye state was measured by the procedure shown in (1).

(4) On the 5th day from the start of instillation, the dry eye state was measured by the procedure shown in (1).

Calculation of Tear Film Break-Up Area

At the time point when the rabbit dry eye model was generated, an image was acquired. The acquired image was captured with image processing software Image J, and an area in which a tear was broken up was calculated (initial value).

For the rabbit dry eye model, images were acquired again after 2 days and after 5 days from the start of instillation to each of the above-mentioned model (I), the above-mentioned model (II), the above-mentioned model (III), and the above-mentioned model (IV).

The acquired image was captured with Image J, and an area in which a tear was broken up was calculated (after 2 days and after 5 days).

The area in which the tear was broken up serving as the initial value (dry eye model on the 0th day), and the area in which the tear was broken up after 2 days or after 5 days were compared, and were converted into percentages to calculate tear film break-up areas (%).

Example 5

Determination of Dry Eye Therapeutic Effect through Mucin Level Measurement

A mucin level measurement test was carried out in accordance with the following procedure.

(1) Mucin levels were measured using the dry eye model after the carrying out of Example 4 (after the dry eye measurement). From the dry eye model on the 0th day, tears were collected with Schirmer test paper for 5 minutes, and a mucin level contained in the tears was measured using a tear mucin assay kit (manufactured by Cosmo Bio) and adopted as an initial value.

(2) Mucin levels were measured again on the 2nd day and the 5th day.

The mucin level of a normal rabbit (not the dry eye model) was defined as 100, and mucin levels (%) on the 0th day (day of dry eye model generation), the 2nd day (2nd day from the start of instillation), and the 5th day (5th day from the start of instillation) were calculated.

[Evaluation of Retainability on Ocular Surface by Drug Administration to Dry Eye Model and Evaluation of Dry Eye Treatment]

Figure 2:
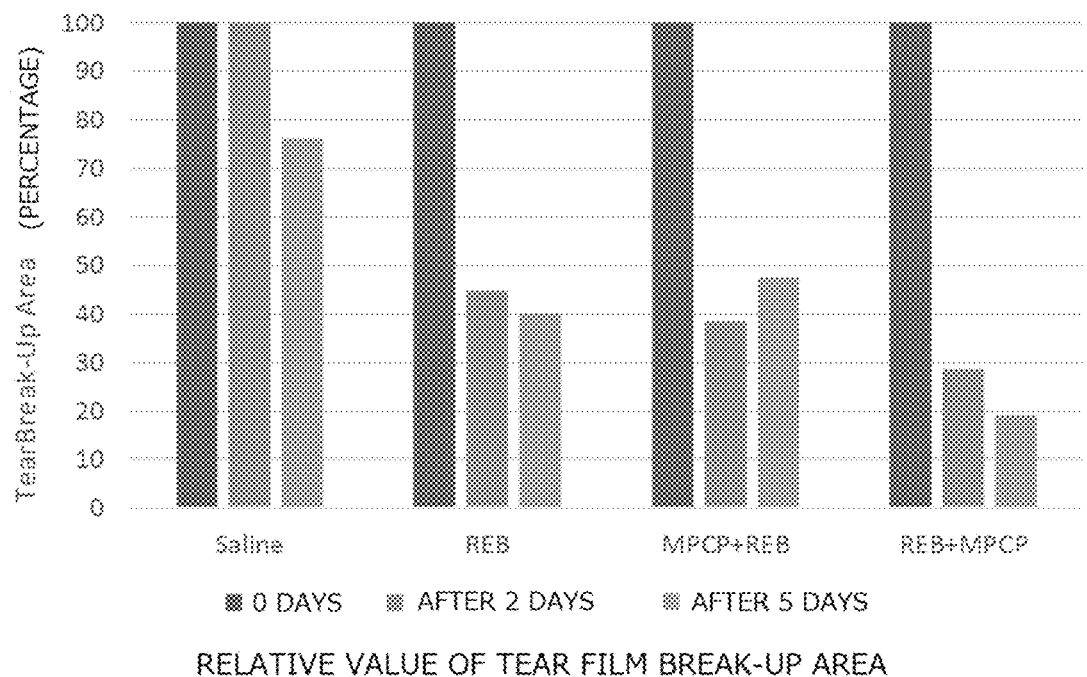
FIG. 2 shows dry eye therapeutic effects on a rabbit dry eye model (measurement of tear film break-up areas). Tear film break-up areas immediately after instillation (0 days: left side), after 2 days (middle), and after 5 days (right side) were measured. For "REB", treatment was performed with an eye drop containing an ophthalmic medicament (rebamipide ophthalmic solution). For "MPCP+REB", instillation treatment was performed with an ophthalmic solution serving as a solution of this Example (ocular surface drug-retaining agent) and the rebamipide ophthalmic solution in the stated order. For "REB+MPCP", instillation treatment was performed with the rebamipide ophthalmic solution and the ophthalmic solution serving as the solution of this Example (ocular surface drug-retaining agent) in the stated order. For "Saline", direct treatment by saline instillation was performed. Calculation was performed with the numerical value of the dry eye model on the 0th day being defined as 100.
Figure 3:
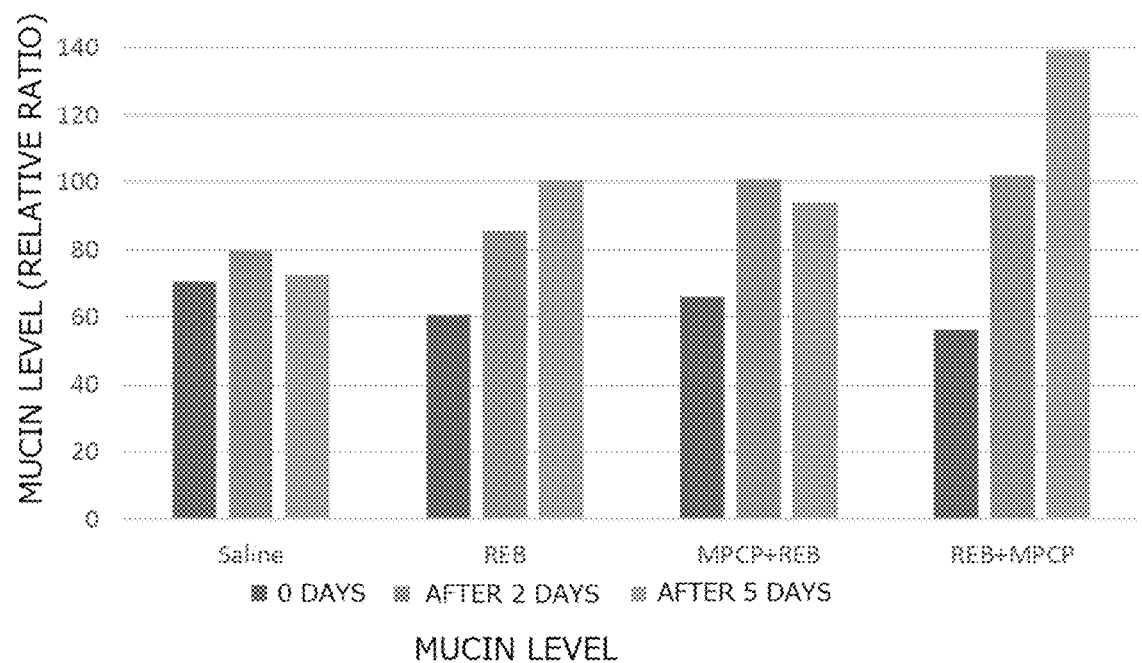
FIG. 3 shows dry eye therapeutic effects on a rabbit dry eye model (measurement of mucin levels). Mucin levels immediately after instillation (0 days: left side), after 2 days (middle), and after 5 days (right side) were measured. For "REB", treatment was performed with an eye drop containing an ophthalmic medicament (rebamipide ophthalmic solution). For "MPCP+REB", instillation treatment was performed with an ophthalmic solution serving as a solution of this Example (ocular surface drug-retaining agent) and the rebamipide ophthalmic solution in the stated order. For "REB+MPCP", instillation treatment was performed with the rebamipide ophthalmic solution and the ophthalmic solution serving as the solution of this Example (ocular surface drug-retaining agent) in the stated order. For "Saline", direct treatment by saline instillation was performed. Calculation was performed with the numerical value of a normal rabbit (not the dry eye model) being defined as 100.

In order to determine the effect of the ocular surface drug-retaining agent of the present disclosure, a retainability measurement test of a drug on an ocular surface and a dry eye therapeutic effect measurement test were carried out. The results of the tests are shown in FIG. 1 to FIG. 3.

Example 6

Temperature Change-associated Viscosity Change

A MPCP solution, a 0.3% diquafosol sodium (DIQ) ophthalmic solution (manufactured by Santen Pharmaceutical Co., Ltd.) serving as a dry eye therapeutic drug, and a 0.1% Hyalein™ ophthalmic solution (manufactured by Santen Pharmaceutical Co., Ltd.), which was a sodium hyaluronate (HYA) ophthalmic solution, serving as a dry eye therapeutic drug were measured for their viscosities using a tuning fork vibration viscometer (A&D Company, Limited). The viscosities were measured at the following two points: 20° C., which is room temperature, and 37° C., which is around a body temperature.

Example 7

Determination of Dry Eye Therapeutic Effect through Calculation of Tear Film Break-Up Area A test was carried out by using a DIQ ophthalmic solution or a HYA ophthalmic solution in place of the rebamipide ophthalmic solution in the procedure of Example 4, and an area in which a tear was broken up, i.e., a tear film break-up area ($mm^2$) was calculated.

Example 8

Determination of Dry Eye Therapeutic Effect through Mucin Level Measurement

A test was carried out by using a DIQ ophthalmic solution or a HYA ophthalmic solution in place of the rebamipide ophthalmic solution in the procedure of Example 5, and a mucin level (%) was calculated.

<Results>

Results of Retainability Measurement Test of Drug on Ocular Surface

The following three kinds were compared in terms of retainability of a drug on an ocular surface: (I) the model subjected to instillation treatment with the rebamipide ophthalmic solution; (II) the model subjected to instillation treatment with the rebamipide ophthalmic solution after the instillation of the ocular surface drug-retaining agent of this Example; and (III) the model subjected to instillation treatment with the ocular surface drug-retaining agent of this Example after rebamipide instillation. (III) The model to which the ocular surface drug-retaining agent of this Example was instilled after rebamipide instillation had high rebamipide concentrations on a corneal surface after 10 minutes from instillation and after 30 minutes from instillation, and had the highest drug-retaining effect (FIG. 1). Thus, it was recognized that the ocular surface drug-retaining agent of this Example was capable of providing an excellent effect of retaining a medicament on the ocular surface (in particular, the corneal surface).

Results of Dry Eye Therapeutic Effect Measurement Test

With regard to the results of the calculation of tear film break-up areas, the model to which the ocular surface drug-retaining agent of this Example was instilled after rebamipide instillation had its dry eye injury ratio reduced to about 20% (FIG. 2). Thus, it was recognized that the ocular surface drug-retaining agent of this Example was capable of providing a sufficient dry eye therapeutic effect and water-retaining effect.

With regard to the results of the mucin level measurement test, the model to which the ocular surface drug-retaining agent of this Example was instilled after rebamipide instillation had its mucin level increased to 140% (FIG. 3). Thus, it was recognized that the ocular surface drug-retaining agent of this Example was able to treat dry eye.

Results of Temperature Change-associated Viscosity Change Test

Figure 4A:
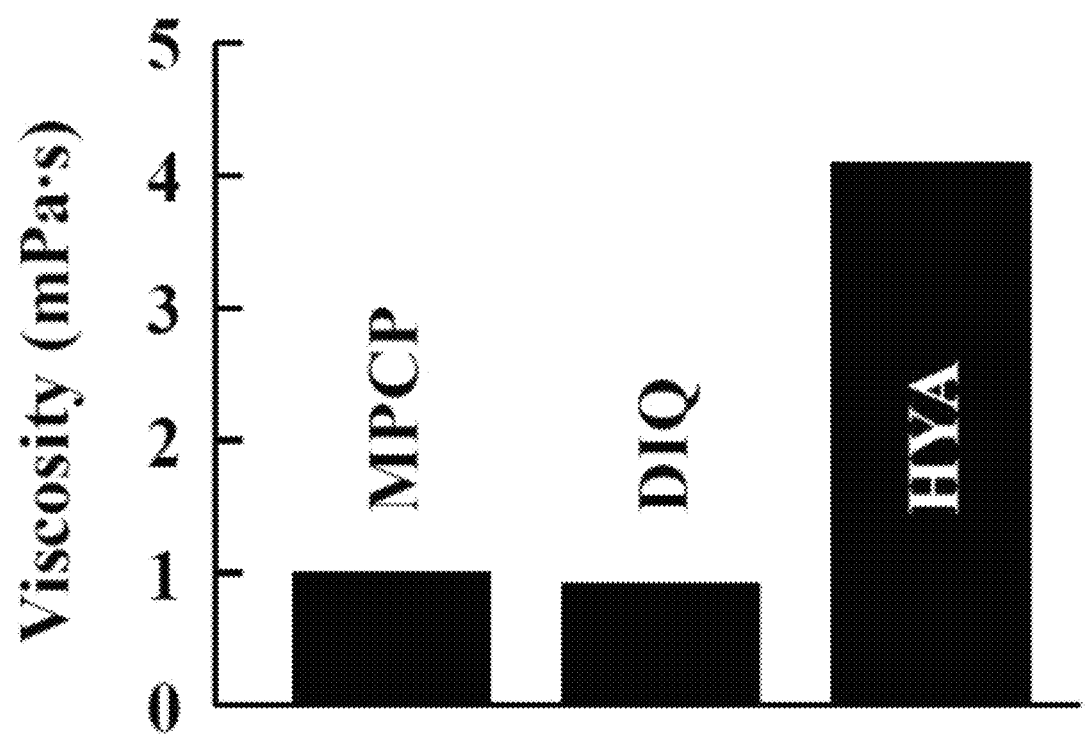
FIG. 4A and FIG. 4B show the results of a temperature change-associated viscosity change test. The viscosity of each eye drop was measured at the following two points: 20° C.
Figure 4B:
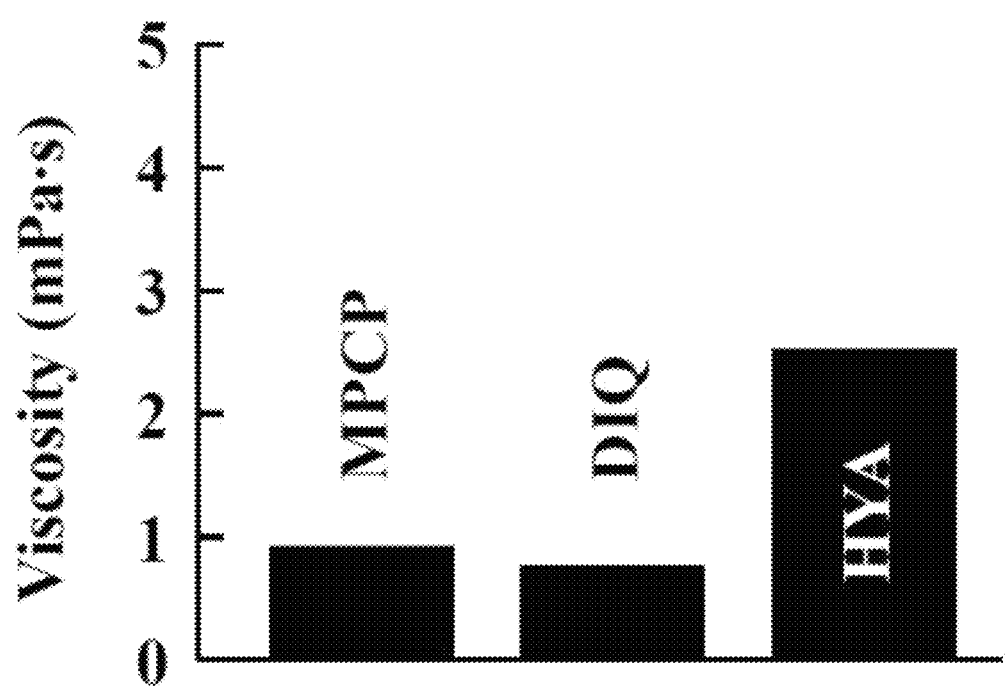
Figure 5A:
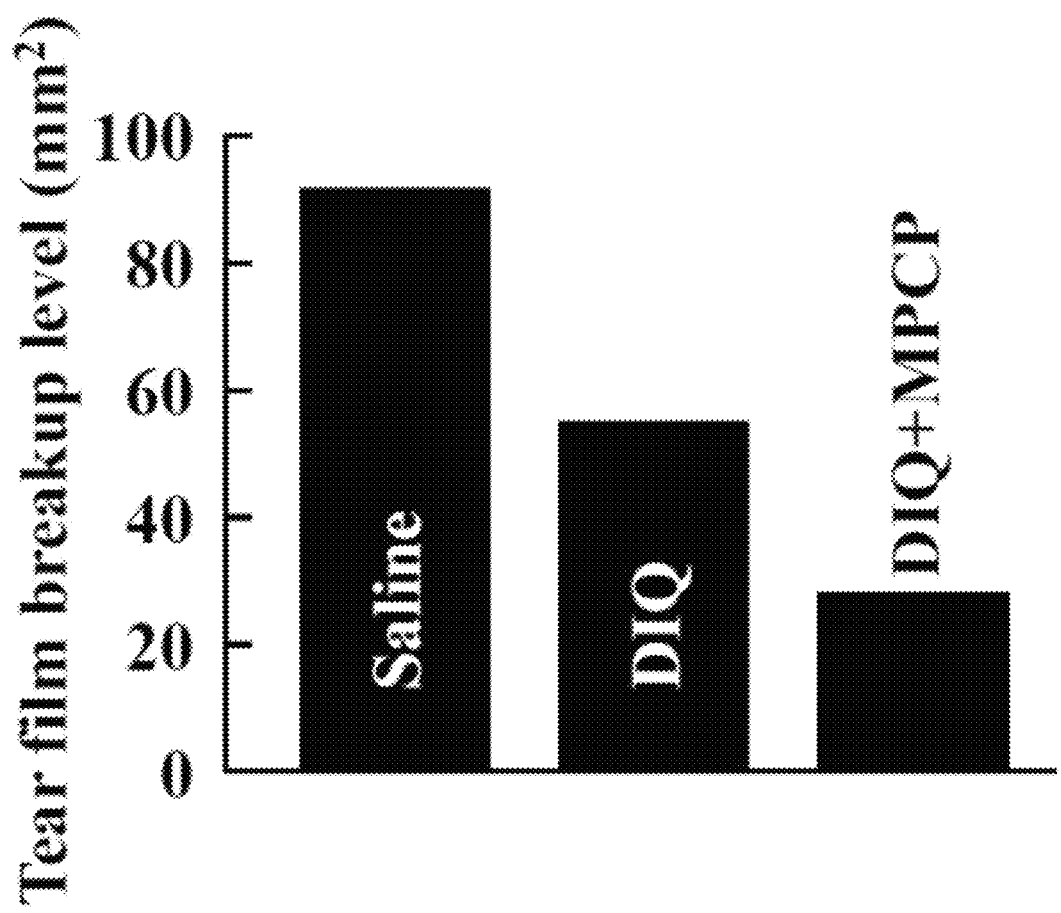
FIG. 5A, FIG. 5B, FIG. 5C, and FIG. 5D show dry eye therapeutic effects on a rabbit dry eye model (measurement of tear film break-up areas). Influences on an ocular surface mucin coating injury model at the time of treatment with a DIQ ophthalmic solution or a HYA ophthalmic solution in combination with a MPCP solution were determined.
Figure 5B:
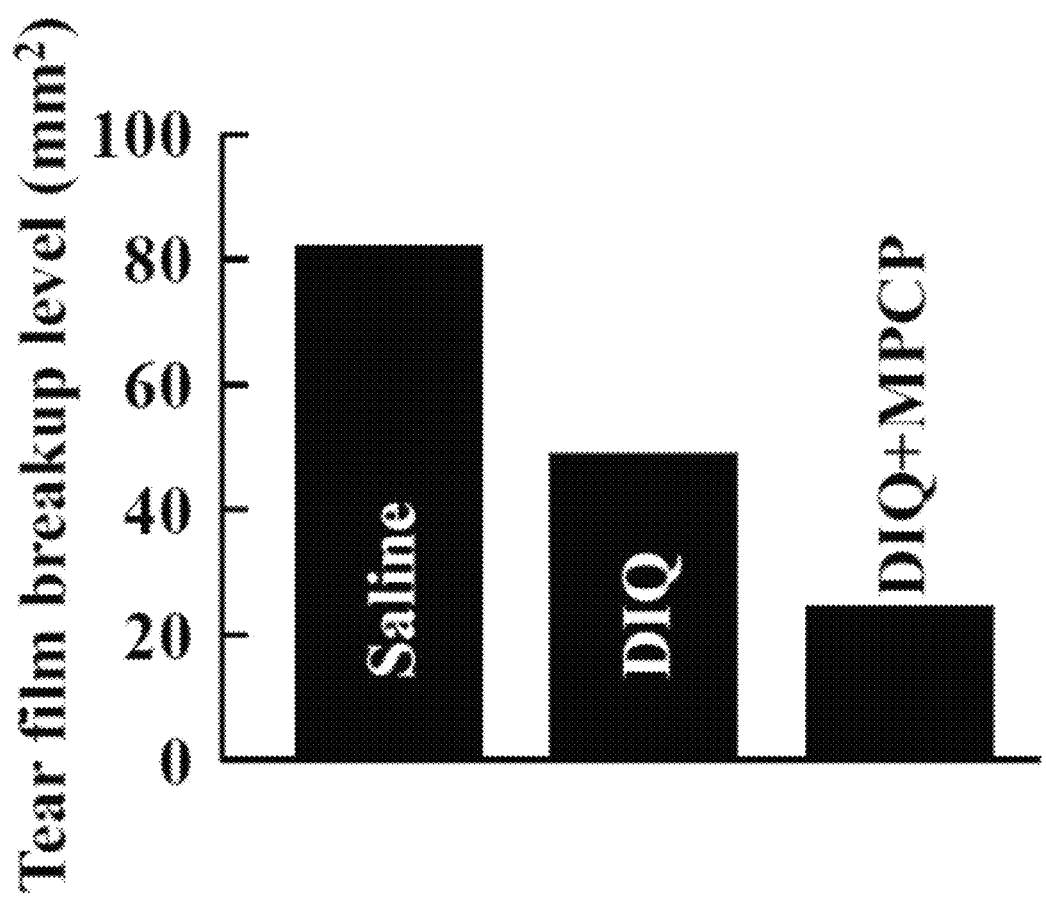
Figure 5C:
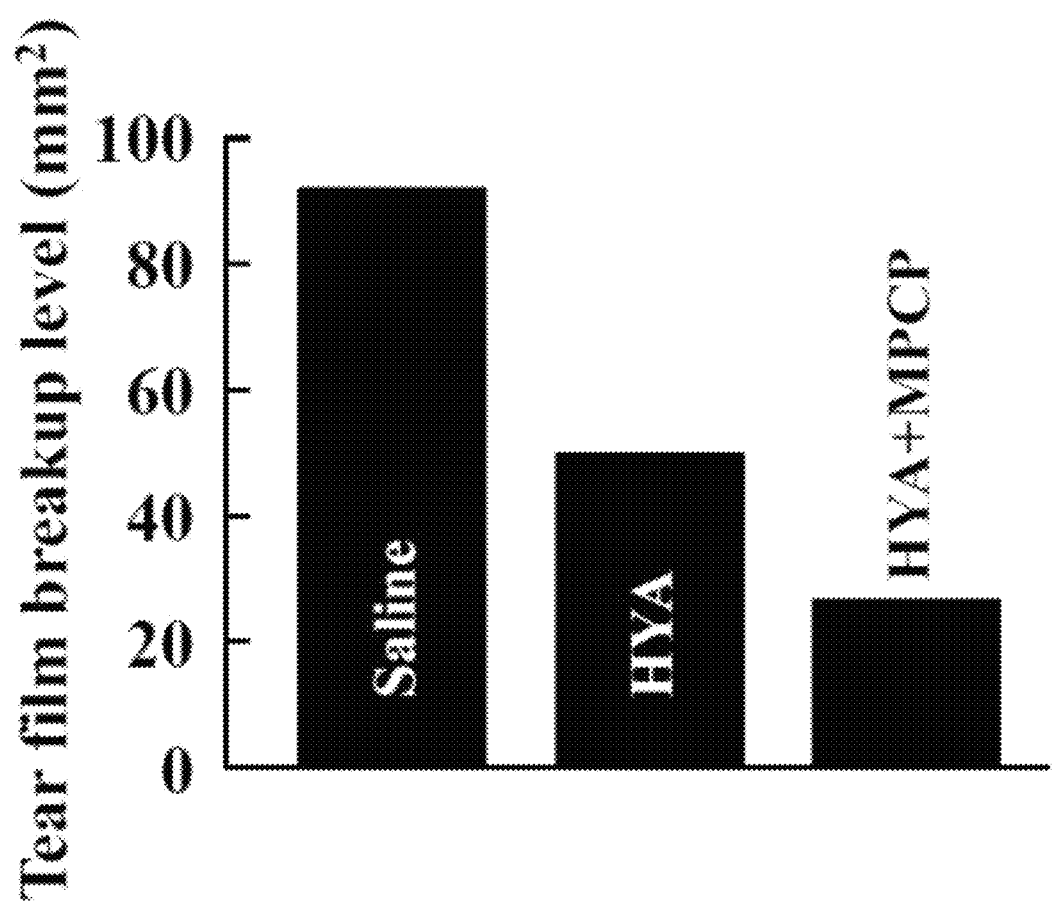
Figure 5D:
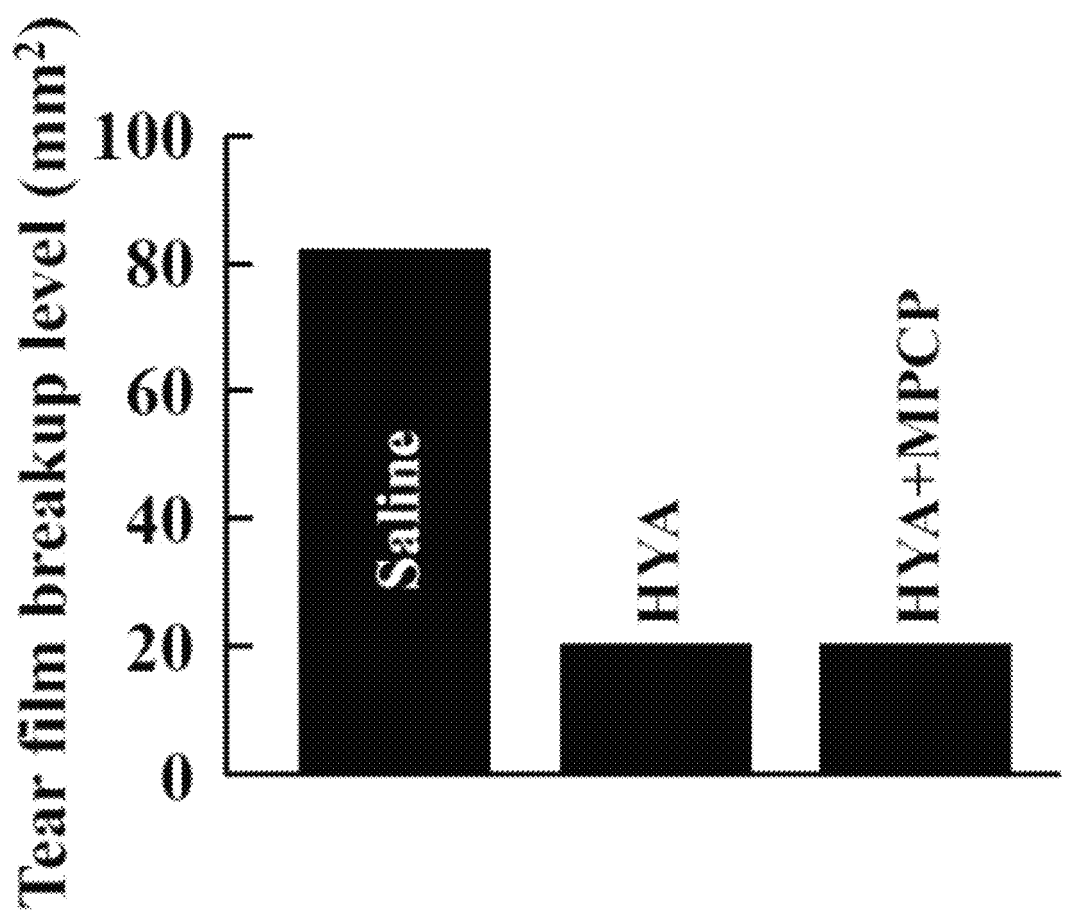
Figure 6A:
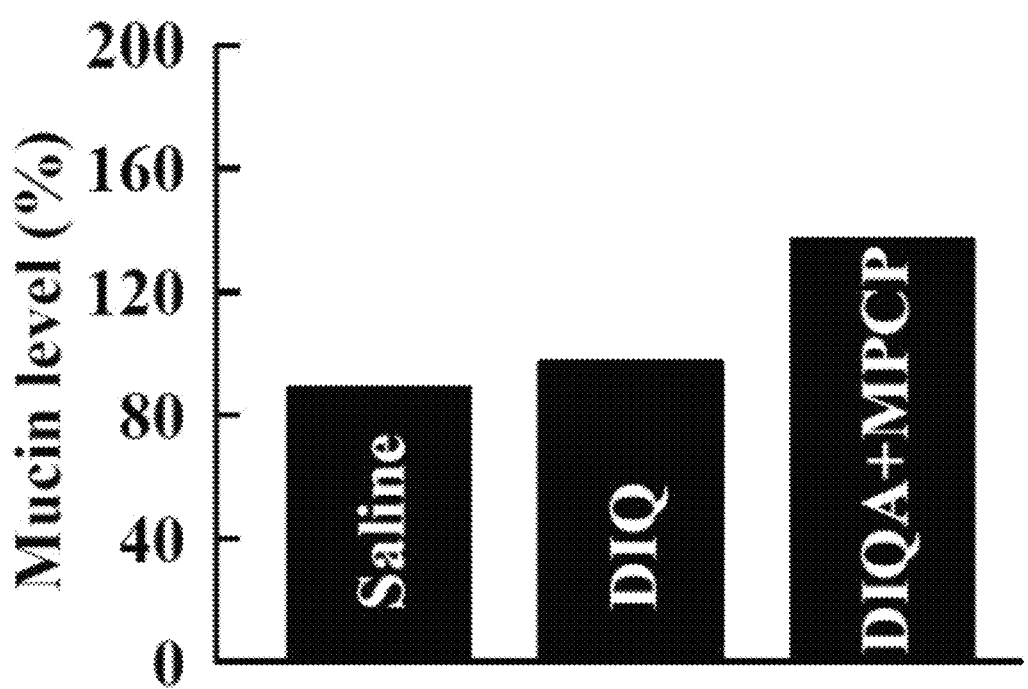
FIG. 6A, FIG. 6B, FIG. 6C, and FIG. 6D show dry eye therapeutic effects on a rabbit dry eye model (measurement of mucin levels). Mucin levels in tears at the time of treatment with a DIQ ophthalmic solution or a HYA ophthalmic solution in combination with a MPCP solution were determined.
Figure 6B:
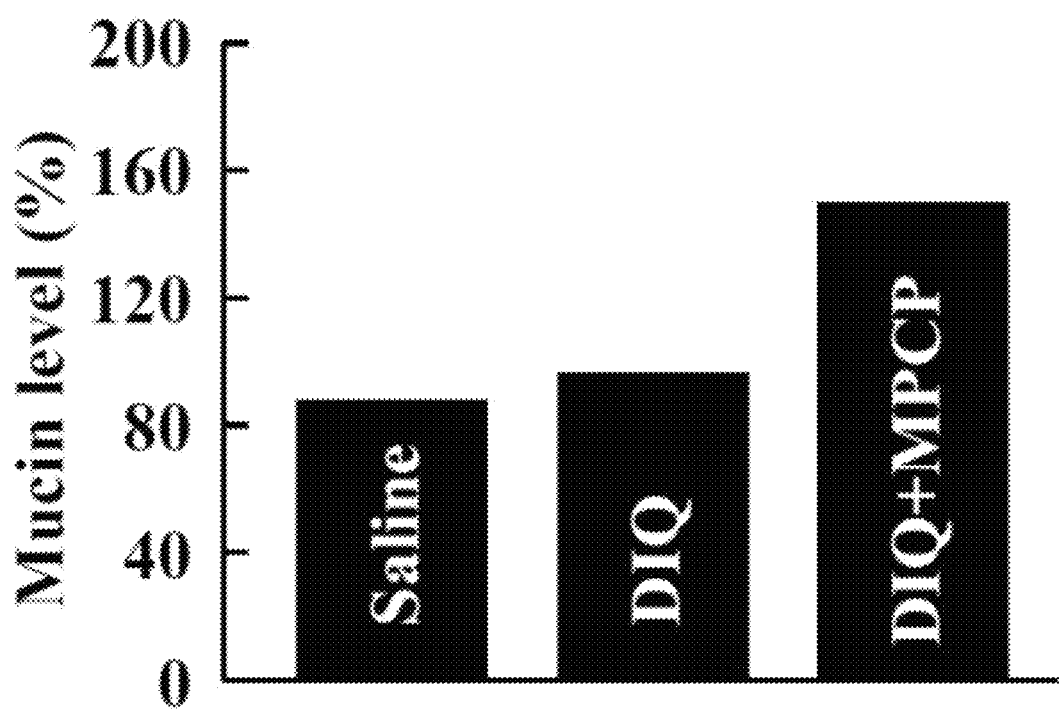
Figure 6C:
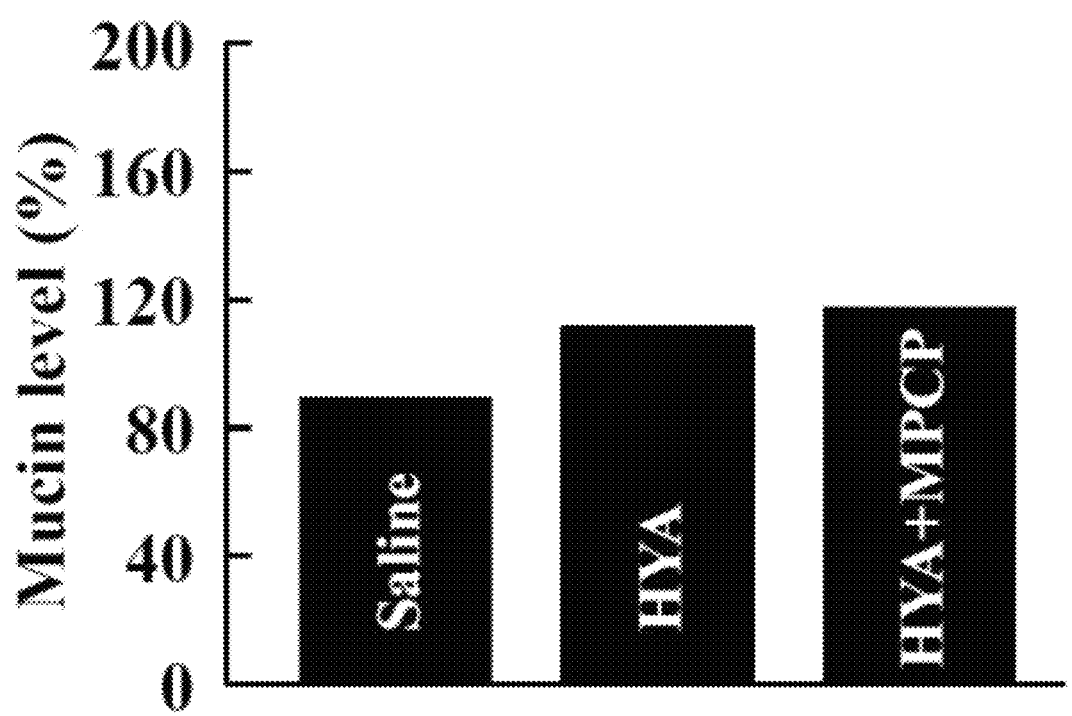
Figure 6D:
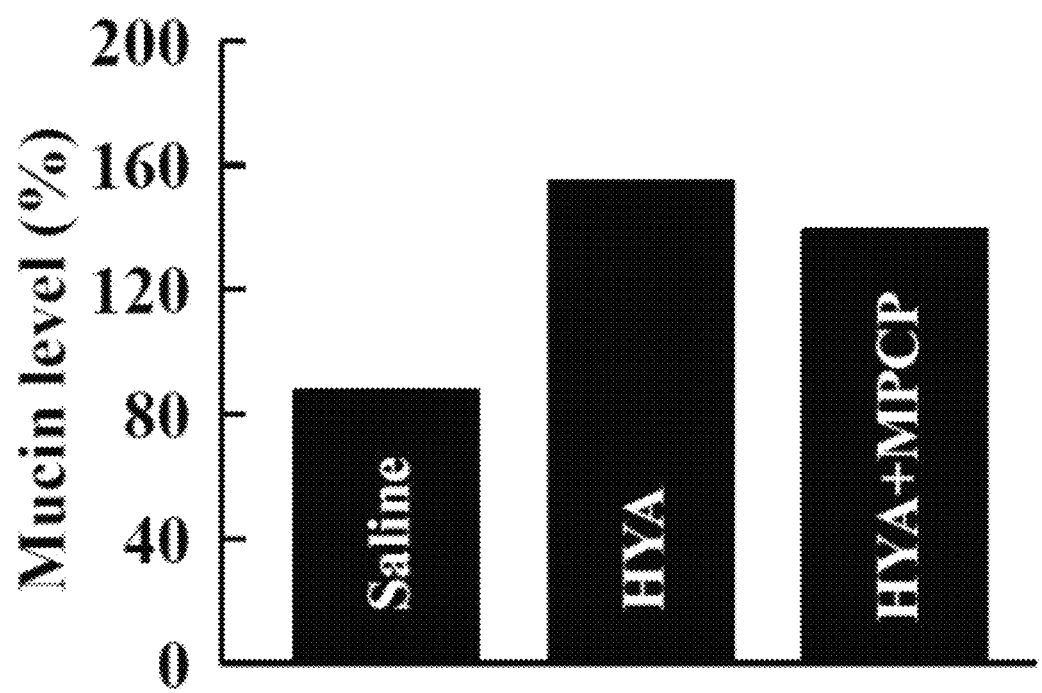

In each of the various solutions, the viscosity tended to be reduced at around the body temperature (37° C.) as compared to room temperature (20° C.), the MPCP solution and the DIQ ophthalmic solution had similar viscosities, and the viscosity of the HYA ophthalmic solution showed high values as compared to the other two agents (FIG. 4A and FIG. 4B).

Thus, it was recognized that the ocular surface drug-retaining agent of this Example was capable of being instilled to an ocular disease patient like a known eye drop.

Results of Dry Eye Therapeutic Effect Measurement Test

When combined treatment was performed with DIQ ophthalmic solution instillation and the MPCP solution, reductions in tear film break-up area after 2 days and after 5 days from instillation were found, and when combined treatment was performed with the HYA ophthalmic solution and the MPCP solution, a reduction in tear film break-up area after 2 days from instillation was found (FIG. 5A, FIG. 5B, FIG. 5C, and FIG. 5D).

Thus, it was recognized that the ocular surface drug-retaining agent of this Example was capable of providing a sufficient dry eye therapeutic effect and water-retaining effect.

Determination of Dry Eye Therapeutic Effect through Mucin Level Measurement

When combined treatment was performed with DIQ ophthalmic solution instillation and the MPCP solution, increases in mucin level in tears after 2 days and after 5 days from instillation were found, and when combined treatment was performed with the HYA ophthalmic solution and the MPCP solution, an increase in mucin level in tears after 2 days from instillation was found (FIG. 6A, FIG. 6B, FIG. 6C, and FIG. 6D).

Thus, it was recognized that the ocular surface drug-retaining agent of this Example was able to treat dry eye.

The ocular surface drug-retaining agent of the present disclosure can allow a drug to be sufficiently retained on an ocular surface or a corneal surface, and moreover, can enhance the sustainability of the effect of the drug.

It has been recognized that the ocular surface drug-retaining agent and the method of retaining a drug on an ocular surface of the present disclosure can allow an active ingredient (ophthalmic medicament) to be retained on an ocular surface. Further, it has been recognized that the ocular surface drug-retaining agent of the present disclosure has an effect of sustaining the effect or action of the active ingredient of the eye drop for treating an ocular disease over a long period of time.

In addition, it has been recognized that the method of treating an ocular disease of the present disclosure can treat dry eye.

What is claimed is:

1. A method of retaining a drug on an ocular surface, comprising administering, to a mammal, an eye drop for treating an ocular disease, and a composition containing 0.001 w/v % to 1.0 w/v % of a copolymer (P) which consists of constituent units represented by the following general formulae (1a) to (1c), has a weight-average molecular weight of from 5,000 to 2,000,000, and has a molar ratio among the constituent units (1a):(1b):(1c) of 100:from 10 to 400:from 2 to 50:

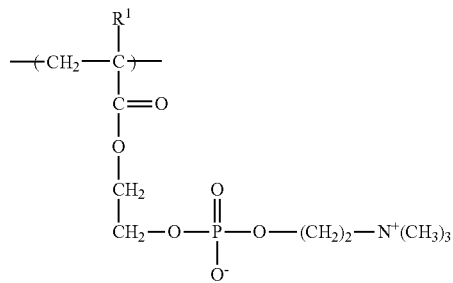

in the general formula (1a), $R^1$ represents a hydrogen atom or a methyl group;

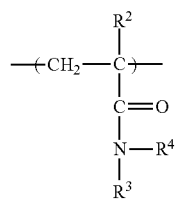

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other, and

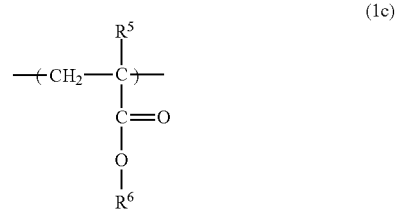

in the general formula (1c), $R^5$ represents a hydrogen atom or a methyl group, and $R^6$ represents a hydrocarbon group having 12 to 24 carbon atoms.

2. The method of retaining a drug on an ocular surface according to claim 1, wherein the composition is administered after the eye drop for treating an ocular disease is administered.

3. The method of retaining a drug on an ocular surface according to claim 1, wherein the eye drop for treating an ocular disease is rebamipide.

4. The method of retaining a drug on an ocular surface according to claim 1, wherein the eye drop for treating an ocular disease is diquafosol sodium.

5. The method of retaining a drug on an ocular surface according to claim 1, wherein the eye drop for treating an ocular disease is sodium hyaluronate.

6. A method of treating an ocular disease, comprising administering, to a mammal, an eye drop for treating an ocular disease, and a composition containing 0.001 w/v % to 1.0 w/v % of a copolymer (P) which consists of constituent units represented by the following general formulae (1a) to (1c), has a weight-average molecular weight of from 5,000 to 2,000,000, and has a molar ratio among the constituent units (1a):(1b):(1c) of 100:from 10 to 400:from 2 to 50:

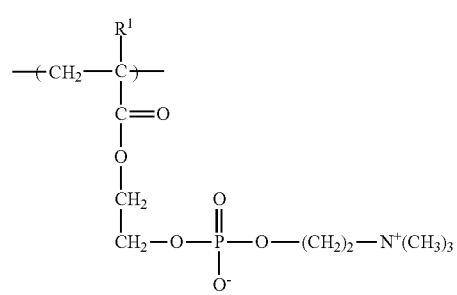

in the general formula (1a), $R^1$ represents a hydrogen atom or a methyl group;

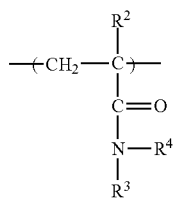

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other, and

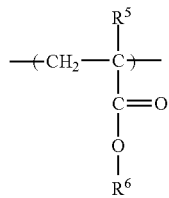
(1c)

in the general formula (1c), $R^5$ represents a hydrogen atom or a methyl group, and $R^6$ represents a hydrocarbon group having 12 to 24 carbon atoms.

7. The method of treating an ocular disease according to claim 6, wherein the composition is administered after the eye drop for treating an ocular disease is administered.

8. The treatment method according to claim 6, wherein the eye drop for treating an ocular disease is rebamipide, and wherein the ocular disease is dry eye.

9. The treatment method according to claim 6, wherein the eye drop for treating an ocular disease is diquafosol sodium, and wherein the ocular disease is dry eye.

10. The treatment method according to claim 6, wherein the eye drop for treating an ocular disease is sodium hyaluronate, and wherein the ocular disease is dry eye.

11. The treatment method according to claim 6, wherein the ocular disease is short tear film break-up time-type dry eye.

12. The method of retaining a drug on an ocular surface according to claim 1, wherein the mammal is a human.

13. The method of treating an ocular disease according to claim 6, wherein the mammal is a human.

* * * * *